United States Patent [19]

Doorakian et al.

[11] Patent Number: 4,540,823
[45] Date of Patent: Sep. 10, 1985

[54] TETRAHYDROCARBYL PHOSPHONIUM SALTS

[75] Inventors: George A. Doorakian, Bedford; Joseph W. Hanafin, Framingham, both of Mass.

[73] Assignee: The Dow Chemical Company, Midland, Mich.

[21] Appl. No.: 620,976

[22] Filed: Jun. 15, 1984

Related U.S. Application Data

[62] Division of Ser. No. 515,824, Jul. 21, 1983, Pat. No. 4,477,645.

[51] Int. Cl.$^3$ .............................................. C08G 59/00
[52] U.S. Cl. ......................................... 568/10; 568/9; 568/11; 568/17
[58] Field of Search ........................ 568/9, 10, 11, 17

[56] References Cited

U.S. PATENT DOCUMENTS 3,674,854  7/1972  Starnes .
4,102,876  7/1978  Brenner et al. .
4,132,706  1/1979  Doorakian et al. .

OTHER PUBLICATIONS

Kosolapoff et al., Organic Phosphorus Compounds, Wiley-Interscience, N.Y., pp. 330, 332, 333, 351, 345, 348, 361, 362, 293, (1972).

*Primary Examiner*—Helen M. S. Sneed
*Attorney, Agent, or Firm*—Michael L. Glenn

[57] ABSTRACT

Novel advanced epoxy resins are prepared using phosphine or phosphonium salt initiators bearing at least one hydroxyphenyl or thiophenyl groups. These phosphonium salt initiators are novel compositions of matter. The resulting resins contain reduced quantities of extractable phosphorus containing moieties.

4 Claims, No Drawings

TETRAHYDROCARBYL PHOSPHONIUM SALTS

CROSS-REFERENCE TO RELATED APPLICATIONS

This is a divisional of application Ser. No. 515,824, filed July 21, 1983, now U.S. Pat. No. 4,477,645.

BACKGROUND OF THE INVENTION

This invention relates to novel tetrahydrocarbyl phosphonium salts and the use of these and other salts to prepare novel epoxy resins. More particularly, the resulting resins incorporate the phosphonium salts or derivatives thereof.

Epoxy resins have long been produced by the reaction of a vicinal epoxide with a compound bearing phenolic hydroxyls in the presence of a catalyst in a so-called advancement reaction. A variety of catalysts have been reported in the art, including tertiary amines, quaternary ammonium halides, phosphonium halides, phosphonium carboxylates and the like. Processes for using these catalysts, as well as stoichiometric reagents, have been detailed in U.S. Pat. Nos. 2,216,099; 2,633,458; 2,658,855; 3,377,406; 3,477,990; 3,547,881; 3,547,885; 3,569,374; 3,694,407; 3,738,862; 3,948,855; 4,048,141; 4,177,216 and 4,302,574. Canadian Pat. No. 893,191, German Patent DT Nos. 2,206,218 and 2,335,199, the texts *Handbook of Epoxy Resins* by H. Lee and K. Neville, McGraw-Hill (1967) and *Epoxy Resins Chemistry and Technology*, edited by C. A. May and Y. Tanaka, Marcel Decker, Inc. (1973) are also of interest.

The use of certain phosphonium trifluoroacetate salts as advancement catalyts for epoxy resins is disclosed in U.S. patent application Ser. No. 391,094, filed June 23, 1982. It is disclosed therein that these phosphonium salts may bear hydroxyphenyl or thiophenyl moieties. It should be noted that the hydroxyphenyl and thiophenyl were proposed by one of the inventors of the instant invention common to the above-identified application.

In general, the prior art catalysts or derivatives thereof can be extracted from the resulting epoxy resin product. In certain applications the presence of an extractable salt is undesirable. Accordingly, it would be desirable to prepare advanced epoxy resin compositions which contain reduced quantities of extractable residue from the catalyst.

SUMMARY OF THE INVENTION

It has now been discovered that a trihydrocarbyl phosphine or quaternary phosphonium cation each of which bear on the average per molecule more than one moiety corresponding to the formula

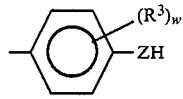

wherein Z is —O— or —S—, $R^3$ at each occurrence is independently, an inert substituent other than —H, e.g., $C_1$ to $C_4$ alkyl or —Cl or —Br, and w is an integer from 0 to 4, promote the reaction of polyepoxides with polyhydric phenols, thiophenols, carboxylic acids or acid anhydrides; yet these phosphorus compounds are not readily extracted from the resulting resins. By the term inert substituent is meant a substituent inert in the instant reaction. Preferably, less than 25 weight percent of the phosphorus compounds initially present in the resulting resin are extracted in refluxing methanol in 12 hours.

The aforementioned phosphinophenols, phosphinothiophenols and quaternized derivatives thereof are incorporated into the resulting resins via reaction with the epoxides. Inasmuch as these phosphorus compounds undergo reaction with epoxides in the subject process, they are referred to herein as initiators rather than catalysts. The resins incorporating moieties derived from these phosphorus compounds are also believed novel.

DETAILED DESCRIPTION OF THE INVENTION

Phosphinophenols, Phosphinothiophenols and Quaternary Derivatives

Preferred phosphorus-containing initiators correspond to one of the following formulae I, II and III:

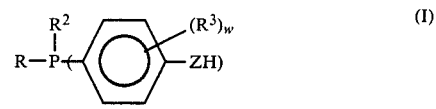

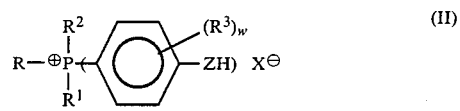

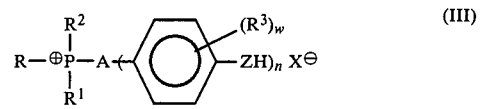

wherein R and $R^2$ are each independently

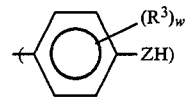

or monovalent hydrocabon radicals, $X^\ominus$ is a compatible anion, $R^1$ is a monovalent hydrocarbon radical optionally including chlorine, bromine, phosphine, phosphonium, phenyl and thiophenyl moieties, Z is independently —O— or —S— at each occurrence, and A is a hydrocarbon radical bearing valences on one or more carbon atoms equal in total to (n+1), where n is an integer 1, 2 or 3.

The compounds of formula II are believed novel. Likewise, the compounds of formula III are believed novel. The compounds of formula I wherein Z is —S— are also believed novel.

These salts of formulae II and III can also be novel zwitterions, i.e., the anion is formed by deprotonation of one of the

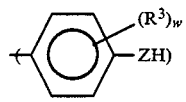

groups. In one preferred embodiment of the invention the initiator corresponds to the formula

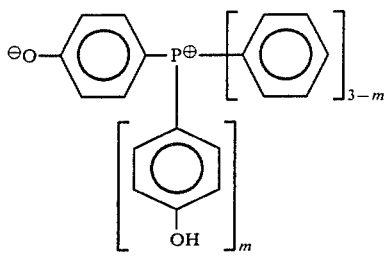

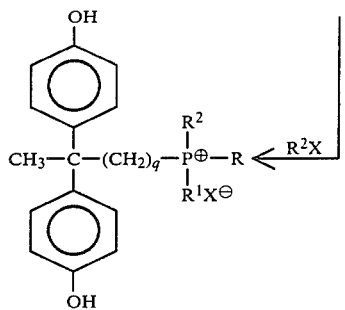

wherein m is an integer from 1 to 3, preferably 1 to 2.

Preferred initiators correspond to formulae I, II or III presented hereinbefore. Particularly preferred are compounds wherein R and $R^2$ are each independently phenyl, thiophenyl or hydroxyphenyl; $R^1$ is phenyl or $C_1$ to $C_4$ alkyl; A is an (n+1)-valent alkyl radical having 1 to 12 carbon atoms; n is 2; w is 0, and $X^\ominus$ is fluoride, bromide, chloride, iodide, carboxylate (such as acetate), bicarbonate, biphosphate, phenate or bisphenate anion. Preferably, each initiator bears a total of two hydroxyphenyl or thiophenyl moieties. Initiators bearing only one hydroxyphenyl or thiophenyl group produce resins of low molecular weight, whereas those bearing more than two such groups produce cross-linked resins when employed at high concentrations. Most preferably, Z at each occurrence in formulae I, II and III is —O—.

These initiators in general can be prepared by techniques known in the prior art. For example, Senear et al, *J. Org. Chem.*, 25, pp. 2001–2006 (1960), describe the preparation of certain compounds corresponding to Formula I and II.

Preferred compounds of Formula III can generally be prepared by the following reaction:

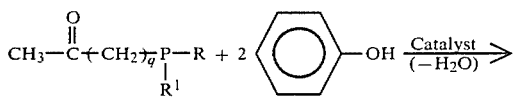

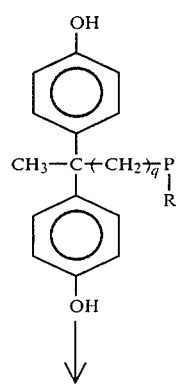

wherein q is an integer from 1 to 20 and the catalyst can be $BF_3$.

The compounds of formula III can also generally be prepared by the following reaction:

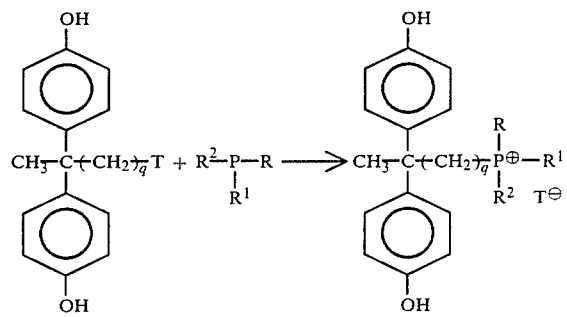

wherein q is an integer from 1 to 20 and T is Cl or Br. Anion exchange is possible to produce salts with other anions.

Still other compounds of formula III can typically be prepared by the following reaction:

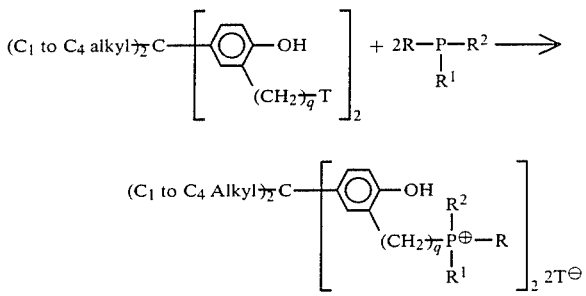

wherein q and T are as described hereinbefore.

The aforementioned reactions are in general conducted neat or in diluents inert in the subject reactions. Preferred as diluents are aromatic hydrocarbon, e.g., xylene. Temperatures from about 25° to about 180° C. are in general suitable for the preparation of the subject initiators.

One of ordinary skill in the art familiar with G. M. Kosolapoff et al, *Organic Phosphorus Compounds*, Vols. 1 and 2, Wiley-Interscience (1972) can readily devise methods of producing other initiators.

The phosphinophenols and their quaternary derivatives are generally white or light-yellow crystalline solids. These solids are generally soluble or slightly soluble in moderately polar solvents.

General Utility:

The subject initiators can be reacted with vicinal epoxide reactants in the same manner as other phenol or thiophenol reactants, except that these initiators do not require a separate catalyst when used at catalytically effective loadings. In preferred embodiments of this invention, other polyhydric phenols not containing phosphorus moieties would be reacted with the epoxide present at the same time as the initiators.

Epoxy Reactants:

The most useful epoxides for reaction with the subject initiators are the polyepoxides, particularly epoxy resins. These polyepoxides are reacted with polyhydric phenols (compounds having more than one phenolic hydroxy group) to form a phenolic hydroxy ether in a so-called advancement reaction. The polyepoxide reactants are organic compounds possessing more than one 1,2-epoxide group per molecule. These polyepoxides can be saturated or unsaturated aliphatic or cycloaliphatic, aromatic or heterocyclic in nature. Additionally, the polyepoxides can bear substituents which are inert in the advancement reaction, such as ether or halogen moieties.

The polyepoxides are conveniently described in terms of epoxy equivalent values, as defined in U.S. Pat. No. 2,633,458. The polyepoxides used in the subject advancement reaction are those having an epoxy equivalency greater than 1.0.

Various examples of polyepoxides that may be used in the invention are given in U.S. Pat. No. 2,633,458 and it is to be understood that so much of the disclosure of that patent relative to examples of polyepoxides is incorporated by reference into this specification.

Other examples of polyepoxides include the glycidyl ethers of novolac resins, i.e., phenol-aldehyde condensates. Preferred resins of this type are those of the formula IV:

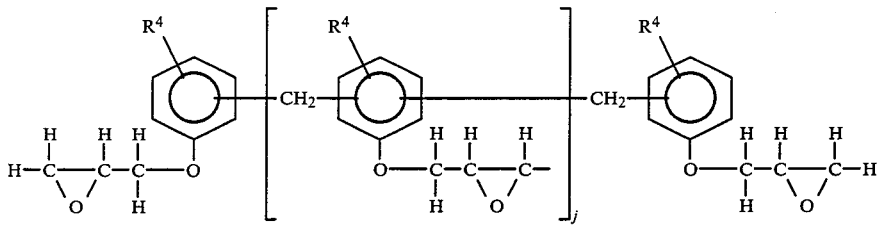

wherein each $R^4$ independently is hydrogen or an alkyl radical and j has an average value of from about 0.1 to about 10, preferably from about 1 to about 2. Preparation of these polyepoxides is illustrated in U.S. Pat. Nos. 2,616,099 and 2,658,885.

The preferred polyepoxides are those represented by the general formula V:

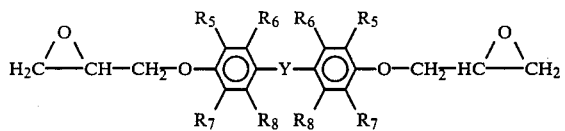

wherein $R_5$, $R_6$, $R_7$ and $R_8$ are each independently selected from hydrogen, bromine, chlorine and —CH$_2$CH=CH$_2$ and wherein Y is selected from oxygen, sulfur, —SO—, —SO$_2$—, bivalent hydrocarbon radicals containing up to about 10 carbon atoms, oxygen-, sulfur- and nitrogen-containing hydrocarbon radicals, such as —OR'O—, —OR'—O—R'—O—, —S—R'—S—, and

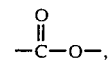

wherein R' is a bivalent hydrocarbon radical at each occurrence. "Y" preferably is an alkylene or alkylidine group having from about 1 to about 4 carbon atoms. In another preferred embodiment, "Y" is derived from the initiators corresponding to formulae I, II or III.

Other examples of polyepoxides include the epoxidized esters of the polyethylenically unsaturated monocarboxylic acids, such as epoxidized linseed, soybean, perilla, oiticica, tung, walnut and dehydrated castor oil, methyl linoleate, butyl linoleate, ethyl 9,12-octadecanedioate, butyl 9,12,15-octadecanetrioate, butyl oleostearate, mono- or diglycerides of tung oil, monoglycerides of soybean oil, sunflower oil, rapeseed oil, hempseed oil, sardine oil, cottonseed oil, and the like.

Other epoxy-containing reactants useful in the disclosed process are obvious to one of ordinary skill in the art. Such reactants are described in U.S. Pat. No. 4,302,574, which is incorporated herein by reference.

Sulfur analogs of glycidyl ether groups, i.e., compounds bearing

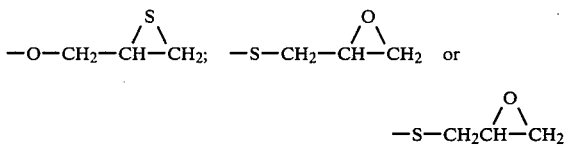

are also operable. For example,

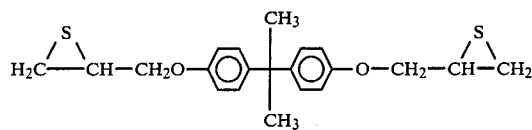

can be used in place of an epoxide reactant.

Phenolic and Thiophenolic Reactants:

The phenolic and thiophenolic reactants are organic compounds having one or more hydroxyl or thiol groups attached to an aromatic carbocyclic nucleus. This class of compounds therefore includes thiophenol, phenol, alpha and beta naphthol, o-, m-, or p-chlorophenol, alkylated derivatives of phenol (e.g., o-methyl-, 3,5-dimethyl-, p-t-butyl- and p-nonylphenol) and other monohydric phenols as well as polyhydric phenols, and as resorcinol, hydroquinone, dithiophenol, p,p'-dimercaptophenyl ether, p,p'-dimercaptobiphenyl, p-hydroxythiophenol, etc.

Mixtures of phenolic and thiophenolic reactants can be employed. However, phenolic reactants are generally preferred.

The polyhydric phenols bearing from 2 to 6 hydroxyl groups and having from 6 to about 30 carbon atoms are particularly useful as reactants in the reaction with epoxy resins to form high molecular weight resins. Representative of these preferred phenols are 2,4',4''-tri(hydroxyphenyl)methane, phenolphthalein and the like. Particularly preferred as phenol reactants are those compounds corresponding to formula V. The most preferred phenols are bisphenol A (4,4'-isopropylidenediphenol), bisphenol F (4,4'-methylenediphenol), 2,2',6,6'-tetrachlorobisphenol A, 2,2',6,6'-tetrabromobisphenol A, bisphenol S (4,4'-sulfonyldiphenol), 4,4'-dihydroxybiphenyl and 2,2'-diallyl bisphenol A. Bisphenol A is the polyhydric phenol of choice.

The subject phosphorus-containing initiators are themselves phenolic or thiophenolic reactants. These initiators comprise up to 100 mole percent of the total phenolic and thiophenolic reactants present, preferably comprise no more than about 10 mole percent of these reactants.

The Carboxylic Acid Reactants:

The organic carboxylic acids and anhydrides are likewise well known. The acids bear one or more carboxyl groups on the organic nucleus. The anhydrides are prepared from such carboxylic acids by the removal of water therefrom in an intra- or intermolecular condensation. This class of compounds therefore includes acetic, propionic, octanoic, stearic, acrylic, methacrylic, oleic, benzoic, phthalic, isophthalic, maleic, succinic, adipic, itaconic, polyacrylic and polymethacrylic acids, and the like, and anhydrides thereof, such as acetic anhydride, phthalic anhydride, hexahydrophthalic anhydride, etc.

A preferred subclass of acids is comprised of members which are useful in cross-linking epoxy resins. The members of this subclass are normally di- or tribasic acids, or anhydrides thereof, and are preferably liquid or low melting solids such as succinic, maleic, or hexahydrophthalic acids or anhydrides and the like. Other such acids and anhydrides are shown, for example, in U.S. Pat. Nos. 2,970,983 and 3,547,885.

Typically, resins prepared from the reaction of epoxides with phenols or thiophenols have more diverse utilities than those prepared from carboxylic acids or anhydrides.

Process for Reacting Epoxide and Phenol:

The reaction conditions employed in the process may be varied. Generally, however, convenient rates of reaction are obtained at reaction temperatures in the range of from about 50° C. to about 300° C. and reaction pressures ranging from about subatmospheric (0.1 millimeter Hg) to about 150 psig.

The ratio of the epoxide to the phenol, thiophenol or carboxylic acid or anhydride reactants to be employed in the process may vary over a wide range depending upon the type of reactants and the type of product desired. For example, if a product terminated with a phenolic hydroxyl group is desired, one would employ an excess of the polyhydric phenol in the process.

The amount of the phosphorus-containing initiator employed in the process of this invention can likewise vary over a wide range, so long as an effective amount is present. In general, the initiator is added in amounts of at least about 0.01 percent, preferably from about 0.1 percent to about 10 percent, by weight of the other reactants.

The reaction may be conducted in the presence or absence of solvents or diluents, but is conveniently conducted in a liquid phase. In most cases, the reactants will be liquid or low melting solids and the reaction may be at least initially easily effected without the addition of solvents or diluents. As the advancement reaction proceeds and the average molecular weight of the product increases, the reaction mixture becomes progressively more viscous and may solidify. To maintain efficient blending of the reaction mixture, it may be necessary to add diluents, increase the temperature of the reaction mixture to the fusion point of the reactants or to utilize very efficient blending means. Suitable diluents are those organic compounds which are inert to the reactants and in the liquid phase at the reaction temperature, for example, ethylene glycol ethyl ether, xylene, toluene, cyclohexane and the like. The diluent is desirably substantially free of impurities which will decrease the activity of the catalyst, such as hydrogen peroxide or uncomplexed transition metal ions and moieties which react with phosphonium ylids, e.g., water, aldehydes and ketones.

If solvents are employed in the reaction and the resulting product is to be used for coating purposes, the solvent may be retained in the reaction mixture. Otherwise, the solvent can be removed by any suitable method such as distillation and the like.

Desirably, substantially equivalent quantities of polyhydric phenol (or thiophenol) and polyepoxide reactants should be employed in the overall reaction (i.e., no more than about 2 percent excess of either reactant). As the reaction between the polyepoxide and the polyhydric phenol approaches completion, it is desirable, but not essential, to introduce sufficient tetrabromobisphenol A to react the vicinal epoxy groups completely and to increase molecular weight of the product in the manner taught in U.S. Pat. No. 4,104,257.

Advancement Reaction Products:

The products obtained by reacting a polyepoxide with a phenol in the presence of the described initiators are phenolic hydroxy ether compounds. Their physical characteristics will depend upon the reactants and proportions employed. In general, the products will vary from liquids to solids, and in the case of the high molecular weight resins will vary from viscous liquids to hard solids. The products will possess an aliphatic OH group formed by each reaction of an epoxide and a phenolic OH group, and can be further reacted through this group if desired. The polyfunctional reactants will also give products terminated in phenolic OH groups and/or epoxy groups, and these will be available for further reaction. For example, if the initiator bears more than two aromatic hydroxyl groups, the product will have branched or cross-linked structure.

The control of the equivalent ratio of the polyepoxides and polyhydric phenols during the advancement reaction permits the preparation of a variety of products. Those products which use an excess of the polyepoxide in their preparation will be terminated in epoxy groups and can be used as polyepoxides in known reactions of polyepoxides with curing agents and the like. The high molecular weight polyepoxides are particularly useful in preparing surface coatings, adhesives, laminates, filament windings, coatings for highways and airfields, structural appllications, formation of foams and the like. Those prepared from the halogenated polyhydric phenols or containing a large weight percentage of phosphorus moieties are particularly useful as flame-proofing resins for forming laminates coatings and the like.

If the advanced resins are prepared under essentially anhydrous conditions (eliminating essentially all water from the reactants) and at temperatures less than about 170° C., the phosphorus moieties though polymer-bound retain catalytic activity. The reaction conditions are further described in U.S. patent application Ser. No. 470,107, filed Feb. 28, 1983. These resins exhibit accelerated curing with amines and anhydrides.

Resins prepared at higher temperatures or in the presence of water will generally contain phosphorus moieties present as polymer-bound tertiary phosphine oxides or phosphonium cations. These moieties exhibit little catalytic activity but improve ignition retardance of the resin.

The reaction products terminated in epoxy groups can also be used to prepare vinyl ester resins. Vinyl ester resins are described in U.S. Pat. No. 3,367,992 wherein dicarboxylic acid half esters of hydroxyalkyl acrylates or methacrylates are reacted with polyepoxide resins. Bowen in U.S. Pat. Nos. 3,066,112 and 3,179,623 describes the preparation of vinyl ester resins from unsaturated monocarboxylic acids such as acrylic and methacrylic acid. Vinyl ester resins based on epoxy novolac resins are described in U.S. Pat. No. 3,301,743 to Fekete et al. Fekete et al also describe in U.S. Pat. No. 3,256,226 vinyl ester resins wherein the molecular weight of the polyepoxide is increased by reacting a dicarboxylic acid with the polyepoxide resin as well as acrylic acid, etc. Other difunctional compounds containing a group which is reactive with an epoxide groups, such as an amine, mercaptan, and the like, may be utilized in place of the dicarboxylic acid. All of the above-described resins, which contain the characteristic linkages

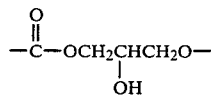

and terminal, polymerizable vinylidene groups, are classified as vinyl ester resins, and are incorporated herein by reference.

The unsaturated monocarboxylic acids which can be reacted with a polyepoxide in the presence of the described catalysts to prepare a vinyl ester resin include acrylic acid, methacrylic acid, halogenated acrylic acid or methacrylic acid, cinnamic acid and the like and mixtures thereof, and hydroxyalkyl acrylate or methacrylate half esters of dicarboxyl acids as described in U.S. Pat. No. 3,367,992 wherein the hydroxyalkyl group preferably has from 2 to 6 carbon atoms.

The products prepared by the reaction of epoxides with thiophenols are generally similar in properties and utilities to those prepared from phenols. Typically, the thiophenol-derived resins exhibit higher molecular weights than their phenolic counterparts.

The following examples are illustrative of the subject invention and are not to be construed as limiting the scope thereof. All parts and percentages are by weight unless otherwise indicated. For the purposes of these examples, the theoretical epoxide content has been calculated neglecting the reaction of the initiator as a phenolic reactant. The inclusion of the initiator as a phenolic reactant in these calculations would increase the theoretical epoxide content slightly, typically about 0.1 percent (e.g., 8.1% instead of 8.0%).

EXAMPLE 1

Magnesium turnings (9.72 gram (g), 0.4 mole) were placed in a 1-liter, 3-neck, round-bottom flask equipped with a condenser and drying tube (CaCl$_2$), addition funnel, magnetic stirrer, and N$_2$ bubbler. The assembly was flame-dried using a Bunsen burner with a constant stream of dry N$_2$ passing through the vessel. Upon cooling to room temperature, 200 ml absolute ether was added, followed by dropwise addition of p-bromoanisole (74.8 g, 0.4 mole) over 30 minutes. When the reaction began to effervesce, it was partially cooled in a salt/ice bath. After 2 hours only traces of magnesium remained and the solution was cooled to $-10°$ C. Phosphorus trichloride (18.3 g, 0.13 mole) in 70 ml ether was then added over 2 hours. The solution was allowed to warm to room temperature overnight, diluted with 300 ml dry toluene, and the ether distilled off. This solution was cooled to 0° C. and NH$_4$Cl (25 g in 100 ml H$_2$O) was added. After 2 hours the toluene layer was separated, dried over MgSO$_4$, filtered, and solvent removed on a rotary evaporator leaving an oil that quickly solidified. Recrystallization from absolute ethanol gave 19 g (47%) white rosettes which were confirmed by conventional analytical techniques to be tri(p-methoxy)phenylphosphine (m.p. 126°–128° C.). NMR (CD$_3$OD); δ(ppm, TMS) 3.60 (s, 3H, CH$_3$), 6.9–7.6 (m, 4H, aromatic).

To 30 ml 48% HBr in a 50 ml round-bottom flask was added 1 gram (0.0033 mole) of tri(p-methoxyphenyl)-phosphine. The homogeneous solution was heated to reflux (124° C.) under a stream of N$_2$ (to remove CH$_3$Br) and within 40 minutes a white precipitate formed. After 2 hours reflux, the mixture was filtered, washed with water, and vacuum dried to give 1.11 g (98%) tri(p-hydroxyphenyl)phosphine hydrobromide.

This hydrobromide salt was stirred in 10 ml 3% NaOH for 1 hour at room temperature. Dry ice (CO$_2$) was added to neutralize excess NaOH and a precipitate quickly formed. This mixture was extracted with 3×50 ml absolute ether, dried over MgSO$_4$, filtered, and ether was removed on a rotary evaporator leaving 0.88 g of tri(p-hydroxyphenyl)phosphine (86%), (m.p. 128°–133° C.). NMR (CD$_3$OD); δ(ppm, TMS) 6.9–7.6 (m, aromatic).

Tri(p-hydroxyphenyl)phosphine (4 g, 1.29 millimole (mmole)) was stirred in 150 ml absolute ether at room temperature in a 250 ml round-bottom flask. Methyl iodide (2.75 g, 19.4 mmol, 1.21 ml) was added, and the solution stirred overnight. A test for unreacted phosphine in the ether solution (maleic anhydride in acetone) was negative, and the product was filtered off as a white precipitate and vacuum dried at room temperature overnight giving 5.76 g of tri(p-hydroxyphenyl)-methylphosphonium iodide (98.8% yield). NMR (CD$_3$OD); δ(ppm, TMS) 2.80 (d, 3H, CH$_3$), 6.82–7.52 (m, 12H, arom.).

EXAMPLE 2

In a manner otherwise similar to Example 1, methyl di(p-hydroxyphenyl)phenyl phosphonium iodide was prepared using phenyldichlorophosphine in place of phosphorus trichloride.

EXAMPLE 3

In a manner otherwise similar to Example 1, methyl(p-hydroxyphenyl)diphenyl phosphonium iodide was prepared using diphenylchlorophosphine in place of phosphorus trichloride.

EXAMPLES 4–7

Tri(p-hydroxyphenyl)phosphine hydrobromide prepared in Example 1 and the products prepared in Examples 2 and 3 were used to promote the reaction of bisphenol A and a commercial epoxy resin (DER-330 ™ epoxy resin sold by The Dow Chemical Company). To a flask equipped with a stirrer, thermometer, heating mantle and nitrogen purge line was charged 224.2 grams of DER-330 ™ epoxy resin and 75.8 grams of bisphenol A. The mixture was heated with stirring to 50° C. and then 0.3 or 3.0 grams of each initiator in 20 milliliters (ml) of methanol were added in separate runs.

The resulting reaction mixtures were heated rapidly to 150° C. at which point heating was discontinued and the reaction allowed to exotherm. After the exotherm had subsided to 160° C., this temperature was maintained for an additional three hours. The products were poured into trays and allowed to cool. The product from the tri(p-hydroxyphenyl)phosphine hydrobromide was very viscous at 160° C., while the other products were free-flowing liquids.

The solid resins were analyzed via conventional methods to determine the final epoxide content. The theoretical epoxide content in each case was 8 percent. A 150-gram sample of each resin was refluxed in methanol overnight in a Soxhlet extractor. The extract was concentrated, dissolved in ethylene glycol ethyl ether to prepare a 50 percent solution and analyzed by phosphorus-31 nuclear magnetic resonance to determine what percentage of the phosphorus present in the resin had been extracted. The results of these experiments are tabulated in Table I:

TABLE I

| Example | Initiator (%) | | Peak Exotherm (°C.) | Observed % Epoxide | Phosphorus Compounds in Extract (% Initial P) |
|---|---|---|---|---|---|
| 4 | $(HO-C_6H_4-)_3P \cdot HBr$ | (1.0%) | 191 | 5.90 | None Observed |
| 5 | $(HO-C_6H_4-)_2P^{\oplus}(-Phenyl)(-CH_3) \; I^{\ominus}$ | (1.0%) | 182 | 6.30 | " |
| 6 | " | (0.1%) | 230 | 8.13 | " |
| 7 | $HO-C_6H_4-P^{\oplus}(-Phenyl)_2(-CH_3) \; I^{\ominus}$ | (1.0%) | 205 | 6.93 | " |

The data presented in Table I indicates that all of these initiators effectively promote reaction of epoxides and phenolic hydroxyls. The phosphorus-containing residue from the initiators was not extractable.

COMPARATIVE EXPERIMENTS 1–3

In a series of comparative experiments, conventional epoxy advancement catalysts were used in place of the initiators in reactions and tests otherwise similar to Example 4. The catalysts were all employed at a loading of 1 weight percent based on the reactants. The catalysts included triphenylphosphine hydrobromide, ethyltriphenylphosphonium iodide and ethyltriphenylphosphonium acetate. The results of these experiments are compiled in Table II:

TABLE II

| Comp. Exp. | Catalyst | Peak Exotherm (°C.) | Observed % Epoxide | Phosphorus Compounds in Extract (% Initial P) |
|---|---|---|---|---|
| 1 | $(Phenyl)_3-P \cdot HBr$ | 195 | 7.60 | $(Phenyl)_3P=O$ (100%) |
| 2 | $(C_2H_5-)P^{\oplus}(-Phenyl)_3 \; HC_3CO_2^{\ominus} \cdot H_3CCO_2H$ | 185 | 7.76 | $C_2H_5-P(=O)(-Phenyl)_2$ (100%) |
| 3 | $(C_2H_5-)P^{\oplus}(-Phenyl)_3 \; I^{\ominus}$ | 179 | 7.17 | $C_2H_5-P(=O)(-Phenyl)_2$ (9.2%); $(Phenyl)_3P=O$ (84.8%) |

It is apparent that phosphorus-containing compositions derived from conventional catalysts can be extracted from epoxy resins made using these catalysts.

EXAMPLE 8

The solid methyl di(p-hydroxyphenyl)phenyl phosphonium iodide prepared in Example 2 was added to excess 1.0 Normal aqueous NaOH and stirred for 15 minutes at 25° C. Solid dry ice was added slowly to precipitate a white solid. This solid was determined by proton magnetic resonance and other conventional techniques to correspond to the formula

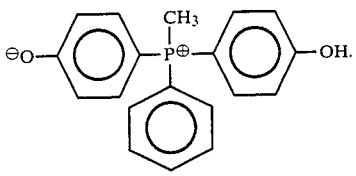

EXAMPLE 9

To a reaction vessel were charged DER-330 epoxy resin and di(mercaptophenyl)ether in a ratio which in theory should produce an advanced resin having 3.0 percent epoxide. To this mixture was added a phenyl di(p-hydroxyphenyl)phosphine initiator in a ratio of 0.5 parts per hundred resin (phr). The advancement reaction was then conducted in the general manner of Example 4.

The resulting resin was determined to contain 2.90 percent epoxide. No phosphorus compounds were extracted from the resin in refluxing methanol.

EXAMPLE 10

To a reaction vessel were charged DER-330 epoxy resin and di(3,3'-allyl-4,4'-hydroxyphenyl)isopropylidene, i.e.,

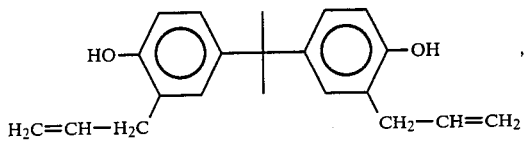

in a ratio which in theory should produce an advanced resin having 8.0 percent epoxide. To this mixture was added the same initiator as in Example 9 in a ratio of 0.2 part phr. The advancement reaction was conducted in the general manner of Example 4.

The resulting resin was determined to contain 7.88 percent epoxide. No phosphorus compounds were extracted from the resin in refluxing methanol.

EXAMPLE 11

To a reaction vessel were charged the same epoxy resin and dihydric phenol as in Example 9 in a ratio which in theory should produce an advanced resin containing 1.0 percent epoxide. To this mixture was added methyl di(p-hydroxyphenyl)phenyl phosphonium acetate in a ratio of 0.4 part phr. The advancement reaction was conducted in the general manner of Example 4.

The resulting resin was determined to contain 1.22 percent epoxide. No phosphorus compounds were extracted from the resin in refluxing methanol.

EXAMPLES 12–21

A series of reactions were conducted in which various polyepoxides and dihydric phenols or thiophenols were reacted in the presence of various initiators in accordance with the general procedure of Example 4. The epoxide content of the resulting resin was determined as well as the percentage of phosphorus which could not be extracted by refluxing methanol. The reactants, initiator, percent epoxide and other parameters or results are tabulated in Table III.

TABLE III

| Example | Epoxide | Phenol | Initiator (phr) | % Epoxide Theoretical | % Epoxide Observed | % Phosphorus Not Extracted |
|---|---|---|---|---|---|---|
| 12 | DER-330* | H—[—⌬—OH / CH₂—CH=CH₂ ]— | H₃C—C(—⌬—OH]₂)(CH₂)₃ / (n-C₄H₉)₃—P⊕ Br⊖ (0.6) | 8.0 | 7.94 | 90% |
| 13 | " | " | H₃C—C(—⌬—OH]₂)(CH₂)₃ / (Phenyl)₃—P⊕ CH₃CO₂⊖ (0.35) | 4.0 | 3.97 | 65% |
| 14 | " | Bisphenol A | H₃C—C(—⌬—OH]₂)(CH₂)₃ / (Phenyl)₃—P⊕ I⊖ (0.35) | 8.0 | 7.95 | 70% |

TABLE III-continued

| Example | Epoxide | Phenol | Initiator (phr) | % Epoxide Theoretical | % Epoxide Observed | % Phosphorus Not Extracted |
|---|---|---|---|---|---|---|
| 15 | " | O+⟨⟩-SH]₂ | H₃C-C(+⟨⟩-OH]₂)(CH₂)₃-(Phenyl)₃-P⊕ I⊖ (0.6) | 1.0 | 1.31 | 70% |
| 16 | " | Bisphenol A | CH₃-⊕P(+⟨⟩-OH]₂)(Phenyl) I⊖ (0.06) | 1.0 | 1.4 | 100% |
| 17 | [⟨⟩-CH₂-CH=CH₂, OCH₂CH-CH₂\O]₂ | [⟨⟩-CH₂-CH=CH₂, OH]₂ | HO-⟨⟩-C(CH₃)(CH₂)₃-⟨⟩-O⁻ P⊕-(Phenyl)₃ (0.4) | 6.0 | 5.82 | 70% |
| 18 | " | " | CH₃-C(+⟨⟩-OH]₂)(CH₂)₃-P⊕-(Phenyl)₃ I⊖ (0.35) | 6.0 | 5.97 | 60% |
| 19 | H-[⟨⟩-OCH₂CH-CH₂\S]₂ | Bisphenol A | Same as in Ex. 18 | N.D. | N.D. | N.D. |
| 20 | " | O+⟨⟩-SH]₂ | " | " | " | " |
| 21 | DER 330* | Bisphenol A | As prepared in Ex. 8 (0.15) | 8.0 | 7.7 | 100 |

*- Trademark of The Dow Chemical Company
N.D. — Not Determined.

What is claimed is:

1. A compound corresponding to the formula

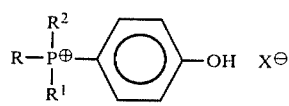

wherein R and R² are each independently phenyl or hydroxyphenyl R¹ is a $C_1$ to $C_4$ alkyl and X⊖ is fluoride, bromide, chloride, iodide, carboxylate, bicarbonate, biphosphate, phenate or bisphenate.

2. A compound corresponding to the formula

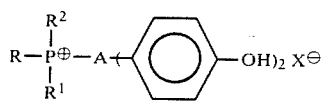

wherein R and R² are each phenyl or hydroxyphenyl R¹ is phenyl or $C_1$ to $C_4$ alkyl A is a trivalent alkane radical having from one to 12 carbon atoms and X⊖ is fluoride, bromide, chloride, iodide, carboxylate, bicarbonate, biphosphate, phenate or bisphenate.

3. A compound corresponding to the formula

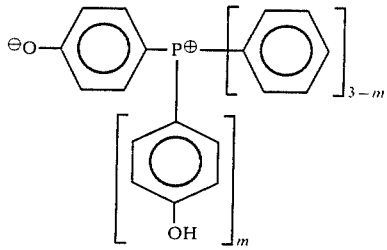

wherein m is an integer from 1 to 3.

4. The compound as described in claim 3 wherein m is the integer 1 or 2.

* * * * *